United States Patent [19]

Homeier

[11] 3,984,478

[45] Oct. 5, 1976

[54] HYDROFORMYLATION PROCESS

[75] Inventor: Edwin H. Homeier, Maywood, Ill.

[73] Assignee: Universal Oil Products Company, Des Plaines, Ill.

[22] Filed: May 27, 1975

[21] Appl. No.: 580,648

[52] U.S. Cl. .................... 260/604 HF; 260/632 HF
[51] Int. Cl.² ......................................... C07C 45/04
[58] Field of Search .............. 260/604 HF, 632 HF, 260/632

Primary Examiner—Jr. Thomas
Assistant Examiner—W. B. Lone
Attorney, Agent, or Firm—James R. Hoatson, Jr.; Raymond H. Nelson; William H. Page, II

[57] ABSTRACT

A hydroformylation process comprising the treatment of an unsaturated compound with carbon monoxide and hydrogen in the presence of a heterogeneous catalyst system comprising a metal selected from the group consisting of a rhenium, rhodium, cobalt, ruthenium, iridium and osmium phthalocyanine compound is disclosed.

11 Claims, No Drawings

HYDROFORMYLATION PROCESS

This invention relates to a process for the preparation of alcohols and aldehydes from the treatment of an unsaturated compound. More specifically, this invention relates to a process for the production of alcohols and aldehydes which comprise the treatment of an unsaturated compound with carbon monoxide and hydrogen in the presence of a heterogeneous catalyst system comprising a metal selected from the group consisting of a rhenium, cobalt, ruthenium, iridium and osmium phthalocyanine compound.

Processes directed to the production of reaction mixtures comprising substantial amounts of aldehydes and alcohols by the hydroformylation of unsaturated compounds with carbon monoxide and hydrogen in the presence of certain catalysts are well known in the art. The aldehydes and alcohols produced generally correspond to the compounds obtained by the addition of a carbonyl or carbinol group to an olefinically unsaturated carbon atom in the starting material or some double-bond isomerized derivative thereof with simultaneous saturation of the olefin bond. The process is known as hydroformylation and involves a reaction which may be shown by the general generic formula:

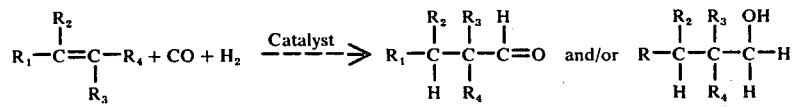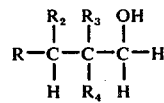

where $R_1$, $R_2$, $R_3$ and $R_4$ may be chosen from a group comprising an organic, halide or hydrogen radical.

It has been shown in the prior art that dicobalt octacarbonyl has generally been used as a catalyst for the hydroformylation of unsaturated compounds. This catalyst, which can be prepared from many forms of cobalt, usually decomposes rapidly at elevated temperatures unless high pressures of about 100–4500 pounds per square inch gauge of carbon monoxide are maintained, depending on the temperature. Another serious disadvantage of hydroformylation processes has been the necessity of proceeding in two steps when alcohols are the desired products. Another disadvantage inherent in the hydroformylation process is the relative inability to direct the reactions involved to the production of predominantly terminal alcohols when the olefins contain more than 2 carbon atoms, particularly when the charge stock to the process comprises primarily internal olefins. Still another and more basic problem in a hydroformylation reaction is the production of a heavy byproduct formation which is worthless and creates a disposal problem. Yet another disadvantage in the hydroformylation processes known to the prior art is the problem of metal recovery in the homogeneous catalyst system.

In contradistinction to the prior art, it has now been shown that the utilization of a heterogeneous catalyst system comprising a metal selected from the group consisting of a rhenium, rhodium, cobalt, ruthenium, iridium and osmium phthalocyanine compound during the hydroformylation of an unsaturated compound by carbon monoxide and hydrogen will add a different dimension to the basic hydroformylation process. The utilization of the present invention will allow the manufacturer an economic advantage over the current processes known to the art as a result of the advantage of more feasible metal recovery when a preferred embodiment of the present invention comprising a supported phthalocyanine compound is utilized as a catalyst. Currently most hydroformylation processes are run in homogeneous systems whereby the metal extraction of cobalt or other various catalytic compounds is difficult to perform. In the process of this invention the phthalocyanine metal catalyst may be supported on an inert support or the catalyst may contact the unsaturated compound in a liquid-liquid two phase reactant-catalyst system, or the catalyst may be present as the neat heterogeneous metal phthalocyanine. These catalyst systems result in a much easier and more beneficial metal catalyst recovery than previously known in the art. The advantage of the recovery of the metal without great expenditure of money follows from the fact that various precious metals such as iridium, rhodium or cobalt are very expensive and the expense of losing the metal catalysts or the expense of recapturing the catalyst must be amortized over the total cost of the alcohols and aldehydes produced in the hydroformylation reaction. The utilization of the above set forth hydroformylation process will also allow for the hydroformylation of unsaturated compounds possessing internal double bonds at lower conditions of temperature and pressure than known before in the prior art. The savings of temperature and pressure will not only save the manufacturer of the alcohols and aldehydes money but also will conserve on precious energy resources necessary in the manufacture of these very desirable oxocompounds.

The desired products to the process of this invention, namely alcohols and aldehydes, are utilized in the chemical industry in many ways. For example, alcohols are utilized in the synthesis of other organic derivatives; as solvents; as an extraction medium; in dyes; synthetic drugs; synthetic rubber; detergents; cleaning solutions; surface coatings; cosmetics; pharmaceuticals; in the preparation of esters; as a solvent for resin in coatings; as a plasticizer; dyeing assistant; hydraulic fluids; detergent formulations; dehydrating agents; or the use of aldehydes as exemplified by their utility as perfumeries or in the synthesis of primary alcohols.

It is therefore an object of this invention to provide a novel process for the preparation of alcohols and aldehydes.

A further object of this invention is to provide an improvement in the process for the preparation of hydroformylation products utilizing certain catalytic compositions of matter which will permit the recovery of the desired hydroformylation compounds and catalytic compositions of matter in a more economically feasible manner.

In one aspect an embodiment of this invention resides in a process for the preparation of hyroformylation products which comprises hydroformylating an unsaturated compound with carbon monoxide and hydrogen in the presence of a heterogeneous catalyst system comprising a metal selected from the group consisting of a rhenium, rhodium, cobalt, ruthenium, iridium and osmium phthalocyanine compound at reaction conditions and recovering the resultant hydroformylated product.

A specific embodiment of this invention resides in a process for preparing 2-n-butylheptanal which comprises hydroformylating decene-5 with carbon monoxide and hydrogen in the presence of a catalyst system comprising chlororhodium phthalocyanine dispersed on a γ-alumina support at a temperature of 80° C. and a pressure of 80 atmospheres of hydrogen and 80 atmospheres of carbon monoxide, said catalytic component comprising 0.1 mols of rhodium per 143.0 mols of decene-5, and recovering the resultant 2-n-butylheptanal.

Another specific embodiment of this invention resides in a process for preparing butyraldehydes by the hydroformylation of propylene in the presence of a cobalt phthalocyanine compound at a temperature of 100°C. and a pressure of 100 atmospheres of hydrogen and 100 atmospheres of carbon monoxide and recovering the resultant butyraldehydes.

Other objects and embodiments will be found in the following further detailed description of the present invention.

As hereinbefore set forth the present invention is concerned with a process for preparing hydroformylated products, namely, alcohols and aldehydes, said process being effected by the hydroformylation of an unsaturated compound with carbon monoxide and hydrogen in the presence of a heterogeneous catalyst system comprising a metal selected from the group consisting of a rhenium, rhodium, cobalt, ruthenium, iridium and osmium phthalocyanine compound. The reaction is effected under hydroformylation conditions which include a temperature in the range of from about 15° C. to about 300° C. and preferably in a range of from about 60° to about 200° C. In addition, another reaction condition involves pressures, said pressures ranging from about atmospheric up to 500 atmospheres or more. The superatmospheric pressures which are employed are afforded by the introduction of gaseous carbon monoxide, hydrogen and, if desired, any substantially inert gas such as nitrogen or helium may also be charged to the hydroformylation zone. Another reaction variable which is employed is the proportional amount of components of the catalyst system present in the hydroformylation process. It is contemplated within the scope of this invention that the heterogeneous catalyst system comprising a metal selected from the group consisting of a rhenium, rhodium, cobalt, iridium and osmium phthalocyanine compound be present in a molar ratio of from about 0.00001 mols of the metal catalyst phthalocyanine compound to about 10.0 mols of the metal catalyst phthalocyanine compound per mol of the unsaturated compound.

Examples of suitable unsaturated compounds which are utilized as the starting material in the hydroformylation process of this invention include, in particular, olefinic hydrocarbons possessing from 3 to 30 carbon atoms, alkyl, carbonyl, carbonyloxy, hydroxy, carboxyl, oxy, amide, amine, nitrile, dienic, or halo-substituted olefinic compounds possessing from about 3 to about 30 carbon atoms, cycloolefinic hydrocarbons possessing from about 5 to about 10 carbon atoms such as propylene, butene-1, butene-2, isobutene, pentene-1, pentene-2, 2-methylbutene-1, 2-methylbutene-2, hexene-1, 3-methylpentene-1, 2-methylpentene-2, heptene-2, 2-methylhexene-2, 3-methylhexene-2, octene-1, octene-2, 3-methylheptene-1, 2-methylheptene-2, nonene-3, 3-methyloctene-2, decene-2, decene-5, 3,4-dimethyloctene-2, 4-ethyloctene-2, undecene-3, undecene-4, 4-methyldecene-2, 4,5-dimethylnonene-2, dodecene-3, tridecene-2, tetradecene-3, pentadecene-5, heptene-1, nonene-1, decene-1, decene-2, decene-3, decene-4, decene-5 undecene-1, dodecene-2, undecene-2, undecene-3, undecene-4, undecene-5, dodecene-1, dodecene-3, dodecene-5, tridecene-1, tridecene-3, tridecene-4, tridecene-6, tetradecene-1, tetradecene-7, pentadecene-1, pentadecene-4, pentadecene-6, 2-methoxybutene-2, 2-methoxypentene-1, 2-ethoxyhexene-1, 1-propoxyheptene-1, 2-ethoxyoctene-1, 2,3-diethoxyundecene-3, hexadecene-1, heptadecene-1, octadecene-1, nonadecene-1, n-eicosene, n-heneicosene, n-docosene, n-tricosene, n-tetracosene, n-pentacosene, n-hexacosene, n-heptacosene, n-octacosene, n-nonacosene, n-tricontene, cyclopentene, cyclohexene, cycloheptene, cyclooctene, cyclononene, cyclodecene, 1-methylcyclohexene-1, 1-ethylcyclohexene-1, 2,3-dipropylcycloheptene-1, 1-methoxycyclopentene-1, 2,3-dipropylcycloheptene-1, 1-chlorocycloheptene-1, 2,3,4-trichlorocyclooctene-1, butyl-2-ene-3-one, penty-2-ene-4-one, hex-1-ene-5-one, oct-2-ene-6-one, non-3-ene-6-one, dec-2-ene-3-one, undec-4-ene-5-one, dodec-4-ene-6-one, tridec-1-ene-5-one, tetradec-1-ene-2-one, pentadec-1-ene-5-one, hexadec-1-ene-5-one, heptadec-2-ene-7-one, eicos-1-ene-5-one, pentacos-3-ene-11-one, 3-butenyl acetate, 2-pentenyl acetate, 3-hexenyl acetate, 2-heptenyl acetate, 3-octenyl acetate, 3-nonenyl acetate, 5-undecenyl acetate, 6-tetradecenyl acetate, 4-hexadecenyl acetate, 6-octadecenyl acetate, 8-heneicosenyl acetate, 10-tetracosenyl acetate, 5-octacosenyl acetate, 12-tricontenyl acetate, but-1-ene-3-ol, pent-2-ene-3-ol, hex-2-ene-4-ol, hept-1-ene-3-ol, oct-2-ene-3-ol, non-3-ene-4-ol, dec-3-ene-4-ol, undec-3-ene-4-ol, dodec-3-ene-4-ol, tridec-4-ene-6-ol, tetradec-1-ene-6-ol, octadec-6-en-8-ol, eicos-3-ene-6-ol, tetracos-6-ene-8-ol, pentacos-6-ene-7-ol, tricont-6-ene-23-ol, 2-buteneoic acid, 2-penteneoic acid, 3-hexeneoic acid, 4-hepteneoic acid, 3-octeneoic acid, 4-deceneoic acid, 5-dodeceneoic acid, 7-tetradeceneoic acid, 7-octadecenoic acid, 6-eicoseneoic acid, 4-tricoseneoic acid, 6-tetracoseneoic acid, 11-nonacoseneoic acid, 13-triconteneoic acid, 2-methoxy but-1-ene, 3-methoxy hex-2-ene, 2-ethoxy oct-1-ene, 4-propoxy dec-2-ene, 6-methoxy undec-3-ene, 5-ethoxy dodec-4-ene, 3-propoxy tridec-3-ene, 5-ethoxy-6-methoxy tetradec-1-ene, 5-methoxy hexadec-5-ene, 4-ethoxy heptadec-1-ene, 12-methoxy heptadec-4-ene, 7,7-dimethoxy nonadec-5-ene, 7,7-diethoxy eicos-6-ene, 6,6-dipropoxy heneicos-5-ene, 5,6-dimethoxy docos-3-ene, 11,12-diethoxy tetracos-5-ene, 1,3-methoxy-12-ethoxy-5,6-dipropoxy tricont-4-ene, 2-buteneamide, 2-penteneamide, 3-hexeneamide, 4-hepteneamide, 3-octeneamide, 4-noneneamide, 4-deceneamide, 4-undeceneamide, 3-dodeceneamide, 4-trideceneamide, 7-tetradeceneamide, 8-pentadeceneamide, 7-hexadeceneamide, 6-heptadeceneamide, 4-octadeceneamide, 3-nonadeceneamide, 4-eicoseneamide, 5-heneicoseneamide, 4-docoseneamide, 5-tricoseneamide, 6-tetracoseneamide, 5-pentacoseneamide, 4-hexacoseneamide, 11-heptacoseneamide, 10-octacoseneamide, 11-nonacoseneamide, 14-triconteneamide, 2-buteneamine, 2-penteneamine, 3-hexeneamine, 3-hepteneamine, 3-octeneamine, 2-noneneamine, 3-deceneamine, 4-undeceneamine, 4- dodeceneamine, 5-trideceneamine, 7-tetradeceneamine, 6-hexadeceneamine, 5-heptadeceneamine, 4-octadeceneamine, 3-nonadeceneamine, 2-eiboseneamine, 6-heneicoseneamine, 5-docoseneamine, 7-tricoseneamine, 7-tetracoseneamine, 6-pentacoseneamine, 7-hexacoseneamine, 7-heptacoceneamine, 8-octacoseneamine, 9-nonacoseneamine, 10-triconteneamine, 3-butenenitrile, 2-pentenenitrile, 1-heptenenitrile, 2-hexenenitrile, 3-octenenitrile, 3-nonenenitrile, 5-decenenitrile, 6-undecenenitrile, 5-tridecenenitrile, 7-tetradecenenitrile, 6-pentadecenenitrile, 7-hexadecenenitrile, 8-heptadecenenitrile, 6-octadecenenitrile, 3-nonadecenenitrile, 2-eicosenenitrile, 5-heneicosenenitrile, 6-docosenenitrile, 6-tricosenenitrile, 7-tetracosenenitrile, 8-pentacosenenitrile, 9-hexacosenenitrile, 5-heptacosenenitrile, 8-octacosenenitrile, 9-nonacosenenitrile, 10-triconteneenitrile, 1,4-butadiene, 1,5-pentadiene, 1,7-tetradecadiene, 1,5-decadiene, 1,4-hexadiene, 1,7-octadiene, 3,15-pentacosadiene, 3,5-tricontadiene, 1-chlorobutene-2, 2-chloropentene-1, 2-bromohexene-2, 2,3-dichlorooctene-1, 3-iodooctene-2, 2-methoxy-3-chlorodecene-2, 3,4-dimethyl-2-chlorooctene-2, or mixtures of linear internal olefinic compounds such as internal olefinic compounds possessing carbon numbers of 8 through 10, 11 through 14 or 15 through 18, etc.

It is contemplated within the scope of the process of the present invention that the hydroformylation reaction may be effected in an inert reaction medium. The inert reaction medium may be both organic or inorganic in nature such as an aqueous reaction medium such as water, an alkaline reaction medium such as sodium hydroxide or a basic reaction medium such as ammonia. The reaction medium may also be organic in nature as exemplified by n-pentane, n-hexane, n-heptane, n-octane, n-nonane, isooctane (2,2,4-trimethylpentane), cyclohexane, methylcyclohexane, benzene, toluene, etc.

The catalytic composition of matter of the present invention comprises a heterogeneous catalyst system comprising a metal selected from the group consisting of a rhenium, rhodium, cobalt, ruthenium, iridium and osmium phthalocyanine compound. The heterogeneous system may be defined as a system in which the catalyst is not in a homogeneous state with the reactant and reaction medium. It is contemplated within the scope of this invention that the heterogeneous catalyst system is physically present as the metal phthalocyanine compound dispersed on an inert support such as γ-alumina, silica, silica-alumina, charcoal, thallia, zirconia, mordenite, faujasite, stibite, and magnesia, although not necessarily with equivalent results, whereby the metal phthalocyanine compound may be recovered from the reaction medium by the known technique of the physical removal of the solid bed from the hydroformylation reaction zone. It is also contemplated within the scope of this invention that the metal phthalocyanine compound be dispersed on an acidic or basic organic ion exchange resin such as a sulfonic acid resin, carboxylic acid resin, phenolic resin or amino resin. The metal phthalocyanine may also be present in the form of a liquid-liquid two phase reactant-catalyst system. In such a phase, which is usually aqueous in nature, the reactant and the metal phthalocyanine compounds are separated by two separate and distinct liquid phases. The contact of the reactant with the catalyst is made at the interface of the two liquid-liquid phases. When the metal phthalocyanine composition of matter is removed from the reaction system the separation may be made by a known physical separation of the liquid-liquid two phase system. The metal phthalocyanine compound may also be present in a neat form. In such a neat form the catalyst metal phthalocyanine is mixed in a hydroformylation medium or is mixed with the unsaturated compound during a stirring process. However, the mixture derived thereby separates into two phases comprising metal phthalocyanine and product phases on standing, permitting recovery of the catalytic component and product phases by known physical separation techniques. In the manufacturing of the various metal phthalocyanine compounds it s contemplated that various ligands may be present in the final catalytic composition of matter. The noted ligands may be any negative valent ion which is present in the precursor of the metal phthalocyanine compound. For instance, chlorine may be present in the rhodium phthalocyanine catalyst as a result of the precursor material comprising rhodium trichloride. The end catalyst would in a fact consist of chlororhodium phthalocyanine. Other ligands are also available in the manufacture of the catalyst such as fluoride, bromide, iodide, phosphorous, phosphines, phosphates, sulfates, arsenates, antimony, nitrates, perchlorates, amine, etc. The metal phthalocyanine selected from the group consisting of a rhenium rhodium, cobalt, ruthenium, iridium, and osmium phthalocyanine compound may also be sulfonated, carboxylated, aminated, hydroxylated, nitrated or chlorinated. Suitable examples of the catalytic composition of matter of the present invention will comprise rhenium phthalocyanine tetrasulfonate, rhodium phthalocyanine tetrasulfonate, cobalt phthalocyanine tetrasulfonate, ruthenium phthalocyanine tetrasulfonate, iridium phthalocyanine tetrasulfonate, osmium phthalocyanine tetrasulfonate, rhenium phthalocyanine trisulfonate, rhodium phthalocyanine trisulfonate, cobalt phthalocyanine trisulfonate, ruthenium phthalocyanine trisulfonate, iridium phthalocyanine trisulfonate, osmium phthalocyanine trisulfonate, rhenium phthalocyanine disulfonate, rhodium phthalocyanine disulfonate, cobalt phthalocyanine disulfonate, ruthenium phthalocyanine disulfonate, iridium phthalocyanine disulfonate, osmium phthalocyanine disulfonate, rhenium phthalocyanine monosulfonate, rhodium phthalocyanine monosulfonate, cobalt phthalocyanine monosulfonate, ruthenium phthalocyanine monosulfonate, iridium phthalocyanine monosulfonate, osmium phthalocyanine monosulfonate, rhenium phthalocyanine carboxylate, rhodium phthalocyanine carboxylate, cobalt phthalocyanine carboxylate, iridium phthalocyanine carboxylate, osmium phthalocyanine carboxylate, rhenium phthalocyanine tetracarboxylate, rhodium phthalocyanine tricarboxylate, cobalt phthalocyanine dicarboxylate, ruthenium phthalocyanine tetracarboxylate, iridium phthalocyanine tricarboxylate, osmium phthalocyanine dicarboxylate, rhenium aminophalocyanine rhodium aminophthalocyanine, cobalt aminophthalocyanine, ruthenium diaminophthalocyanine, iridium triaminophthalocyanine, osmium tetraaminophthalocyanine, rhenium hydroxyphthalocyanine, rhodium dihydroxyphthalocyanine, cobalt trihydroxyphthalocyanine, ruthenium dihydroxyphthalocyanine, iridium hydroxyphthalocyanine, osmium tetrahydroxyphthalocyanine, rhenium nitrophthalocyanine, rhodium dinitrophthalocyanine, cobalt tetranitrophthalocyanine, ruthenium trinitrophthalocyanine, iridium nitrophthalocyanine, osmium dinitrophthalocyanine, chlororhenium phthalocyanine, dichlororhodium phthalocyanine, trichlorocobalt phthalocyanine, tetrachlororuthenium phthalocyanine, dichloroiridium phthalocyanine, chloroosmium phthalocyanine, etc. As hereinbefore set forth, the catalytic composition of the present invention may be present in a range of from about 0.00001 mols of the metal phthalocyanine catalyst to about 10.0 mols of the phthalocyanine catalyst per mol of the unsaturated compound which is hydroformylated to the resultant alcohol or aldehyde. It is to be understood that the aforementioned unsaturated compounds, inert reaction mediums and catalytic compositions of matter are only representative of the type of compounds which may be employed in the present invention that the present invention is not necessarily limited thereto.

The process of this invention may be effected in any suitable manner and may comprise either a batch or a continuous type operation. For example, when a batch type operation is employed, the reactant comprising the unsaturated compound, carbon monoxide and hydrogen are placed in an appropriate apparatus along with a catalyst comprising a heterogeneous catalyst comprising a metal phthalocyanine compound selected from the group consisting of a rhenium, rhodium, cobalt, ruthenium and osmium phthalocyanine compound. The autoclave is sealed, heated to a desired operating temperature and maintained thereat for a predetermined residence time. At the end of this time, which may comprise from 0.5 up to 50 hours or more in duration, the heating is discontinued, the autoclave is allowed to return to room temperature and the autoclave is vented thereby allowing it to return to ambient pressure. The reaction mixture is then recovered, separated from the heterogeneous catalyst system by catalyst recovery methods known to the art and subjected to conventional means of purification and separation, said means including washing, drying, extraction, evaporation, fractional distillation, etc., whereby the desired hydroformylation products, namely, alcohols, aldehydes or alcohol-aldehyde mixtures are recovered from the reaction mixture.

It is also contemplated within the scope of this invention that the hydroformylation process for obtaining the desired alcohols and aldehydes will be effected in a continuous manner of operation. When such type of operation is employed, the reactants comprising the unsaturated compounds are continuously charged to the hydroformylation zone containing a heterogeneous catalyst system comprising a metal phthalocyanine compound selected from the group consisting of a rhenium, rhodium, cobalt, ruthenium, iridium and osmium phthalocyanine compound which may be present as dispersed on a solid support or in an aqueous liquid-liquid two phase reactant-catalyst system or as a neat solid phthalocyanine compound. The hydroformylation zone is maintained at proper operating conditions of pressure and temperature by heat and the admission of requisite amounts of carbon monoxide and hydrogen and any substantially inert gas for effecting the hydroformylation reaction. After completion of the desired residence time, the reactor effluent is continuously withdrawn and subjected to conventional means of separation whereby the desired alcohols, aldehydes or aldehyde-alcohol mixtures are recovered while any unreacted starting material comprising the unsaturated compound, carbon monoxide and hydrogen are recycled to the reaction zone to form a portion of the feedstock or gaseous hydrogen or carbon monoxide stream.

Examples of alcohols and aldehydes which may be prepared according to the process of this invention will include butanol-1, pentanol-1, 3-n-propylpentanol-1, hexanol-1, heptanol-1, octanol-1, nonanol-1, decanol-1, 2-methylbutanol-1, 2-methylpentanol-1, 2-ethylpentanol-1, 2-methylhexanol-1,2-ethylhexanol-1, 2-chloropropanol-1, 3-chlorohexanol-1, 2,3-dichloroheptanol-1, 2-ethyl-3-chlorooctanol-1, butanol, butyraldehydes, pentanal, hexanal, heptanal, 2-n-butylheptanal, octanal, nonanal, decanal, 2-n-amyldecanal, undecanal, 2-methylbutanal, 2-methyloctanal, cyclopentyl carbinol, cyclohexyl carbinol, cycloheptyl carbinol, cyclooctyl carbinol, cyclononyl carbinol, cyclodecyl carbinol, 2-methyl-6-octanone-1-al, 2-ethyl-6-octanone-1-al, 2-ethyl-7-tetradecanone-2-al, 4-formylbutyl acetate, 3-formylbutyl acetate, 4-formyltetradecyl acetate, 3-formyleicosyl acetate, 2-formylhexadecyl acetate, 2-methyl-5-octanol-1-al, 2-ethyl-7-tetradecanol-1-al, 2-methyl-6-undecanol-2-al, 5-formyl octanoic acid, 4-formyl tetradecanoic acid, 6-formyl pentacosanoic acid, 7-formyl hexadecanoic acid, 3-formyl nonanoic acid, 6-methoxytridecanal, 4-ethoxytetradecanal, 3-ethoxypentacosanal, 4-propoxyhexadecanal, 3-methoxynonanal, 4-formyl hexanamide, 3-formyl tetradecanamide, 5-formylundecylamine, 7-formyltetradecylamine, 6-formylpentacosylamine, 3-formylbutanenitrile, 4-formyltetradecanenitrile, 5-formyltetracosanenitrile, mixed hydroxymethylalkanes, mixed formylalkanes, etc.

The following examples are given to illustrate the process of the present invention which, however, are not intended to limit the generally broad scope of the present invention in strict accordance therewith.

EXAMPLE I

In this example a chlororhodium phthalocyanine catalyst was prepared by the following method. Thirteen (13.0) grams (0.1 mols) of phthalonitrile was heated with five (5.0) grams (0.0195 mols) of rhodium chloride hydrate at a temperature of 300° C. in a round-bottom flask. The mixture was heated for a period of time comprising 90 minutes until a deep blue-green color persisted in juxtaposition to a white material within the flask. The contents of the flask were cooled, removed from the flask and mixed with 88 mls of concentrated sulfuric acid over a period of time comprising 60 minutes. The addition of the sulfuric acid resulted in a deep blue solution which was decanted into 176 mls of water in an ice bath. The mixture was allowed to digest for 48 hours at ambient temperature and pressure. The resultant product was recovered by filtration and washing with water until the wash was free of sulfuric acid. The resultant product was air dried for a period of time comprising 48 hours after which 34.0 grams of product was recovered. The crude material was purified by acetone and methanol washings and analyzed by infrared spectroscopy and elemental analysis, said analyses disclosing the desired product to be the chlororhodium phthalocyanine compound.

The above set forth catalyst was used in the following hydroformylation of decene-5 to the aldehyde of 2-n-butylheptanal. A catalyst comprising 0.897 mmols of rhodium as chlororhodium phthalocyanine and a charge stock comprising 178.0 mmols of decene-5 were weighed into an 850 ml glass lined-stainless steel rotating autoclave which was flushed with nitrogen and subsequently sealed. Carbon monoxide was charged to an initial carbon monoxide pressure of 60 atmospheres and hydrogen was charged to an initial pressure of 60 atmospheres, said total pressure being 120 atmospheres. The autoclave was rotated and heated to a temperature of 60° C. and maintained thereat for a period of time comprising 18 hours. After passage of the 18-hour period of time, the autoclave rotation was stopped and the autoclave was allowed to return to room temperature after the termination of the heat. Then the autoclave was vented in a fume hood and flushed with nitrogen to remove any residual carbon monoxide. The reaction product was recovered from the autoclave and analyzed by means of gas-liquid chromatography instrumentation, said analysis disclosed the product to comprise 2-n-butylheptanal with 100% conversion to alcohols and aldehydes.

EXAMPLE II

In this example 5.0 grams of rhodium chloride hydrate (0.0195 mols of rhodium) and a small amount of ammonium molybdate were dissolved in 25 mls of water. The solution was mixed with 65 grams (0.132 mols) of 50% aqueous 4-sulfophthalic acid in an evaporating dish until a uniform red brown color was obtained in the dish. The water was evaporated over a period of time comprising about 12 hours in an oven at a temperature of about 130° C. After the resultant product was allowed to cool, a hard solid was formed which was stirred with 44.0 grams of urea and a small amount of water. After a period of time comprising 2 hours a homogeneous slurry was found to result from the urea addition which upon heating to a temperature of 120° C. resulted in gas evolution from the reaction product. The product was stirred and heated further until the temperature was in excess of 280° C. at which time heating was discontinued. The resultant solid was a blue-green solid weighing about 127.0 grams which was ground and charged to 151.0 grams of trichlorobenzene in a round-bottom flask. After refluxing for a period of time comprising 2 hours at a temperature of 200° C. the refluxing was stopped and the solid was broken up with a spatula and refluxed for an additional 5 hours. The resultant product was recovered by filtration and found to be 120 grams of chlororhodium phthalocyanine tetrasulfonate. The crude chlororhodium phthalocyanine tetrasulfonate was purified by recrystallization from a one molar aqueous hydrochloric acid solution saturated with sodium chloride and then by extraction with denatured alcohol. The purified chlororhodium phthalocyanine was impregnated upon 25 ml of an acid washed, vacuum dried charcoal base by dispersing 0.34 grams (0.30 mmols) of the chlororhodium phthalocyanine tetrasulfonate and the charcoal in 400 mls of methanol. The mixture was allowed to stand for a period of time comprising about 2 to 3 hours. The resultant colorless supernatant was filtered from the carbon and the impregnated sample was washed several times with methanol and subsequently dried.

In Example II, 143.0 mmols of decene-5 and the charcoal-supported chlororhodium phthalocyanine tetrasulfonate catalyst were added to an 850 ml glass lined rotating stainless steel autoclave which was flushed with nitrogen and subsequently sealed. Carbon monoxide was charged to an initial carbon monoxide pressure of 80 atmospheres and hydrogen was charged to an initial hydrogen pressure of 80 atmospheres, said total pressure being 160 atmospheres. The autoclave was then rotated and heated to a temperature of 80° C. and maintained thereat for a period of time comprising 9 hours. After the passage of the 9-hour period of time, the rotation of the autoclave was stopped and it was allowed to return to room temperature after the termination of heat, vented in a fume hood and flushed with nitrogen to remove any residual carbon monoxide. The reaction product was recovered from the autoclave and analyzed by means of gas-liquid chromatography instrumentation, said analysis disclosed the presence of 41.4 percent of 2-n-butylheptanal.

EXAMPLE III

The chlororhodium phthalocyanine tetrasulfonate prepared as described in Example II was impregnated upon high density γ-alumina spheres from an aqueous phase in the following manner. After dispersing 0.10 grams (0.090 mmols) of the chlororhodium phthalocyanine tetrasulfonate in 25 ml of water and covering 25 ml of the γ-alumina spheres with water, the deep blue phthalocyanine dispersion was added to the alumina. After a period of time comprising about 5 hours, the resultant colorless supernatant was filtered from the alumina and the impregnated alumina was washed several times with water and dried under a nitrogen stream for about 20 min.

In Example III, the sample of impregnated alumina described above was used repeatedly in consecutive-batch hydroformylation experiments using decene-5 as the test olefin. In each experiment, the decene-5 charge and the impregnated alumina, which was washed with pentene between uses to remove decene-hydroformylation products, were weighed into the glass liner of an 850 ml rotating, stainless steel autoclave. After flushing the autoclave with nitrogen, it was sealed and pressurized to an initial pressure of 80 atmospheres of carbon monoxide and an initial pressure of 80 atmospheres of hydrogen, said total pressure being 160 atmospheres. The autoclave was then rotated and heated to a temperature of 80° C. and maintained thereat for a period of time comprising 18 hours. After the passage of the 18-hour period of time, the rotation of the autoclave was stopped and it was allowed to return to room temperature after termination of heat. The autoclave was vented in a fume hood and flushed with nitrogen to remove any residual carbon monoxide. The reaction products, comprising the heterogeneous catalyst and the product aldehydes, were separated by pouring off the liquid product. The liquid products were analyzed by means of gas-liquid chromatography instrumentation after each consecutive cycle, said analysis disclosed the presence of the percentages of oxo-aldehydes indicated in Table I below:

TABLE I

| Experiment | Mmols Decene-5 Charged | Decane | Decenes[a] | isoundecyl[b] Aldehydes | Undecanal |
|---|---|---|---|---|---|
| 1 | 150 | 0.4 | trace[c] | 99.6 | 0 |
| 2 | 143 | trace | trace | ~100 | 0 |
| 3 | 167 | 0.2 | 0 | 99.6 | 0.1 |
| 4 | 161 | 0 | 0.2[c] | 99.1 | 0.7 |
| 5 | 167 | 0.2 | 20.8 | 78.2 | trace |
| 6 | 157 | 0 | 63.3 | 36.7 | trace |
| 7 | 136 | 0 | 83.0 | 16.9 | trace |
| 8[d] | 150 | 0.2 | 23.7 | 76.2 | 0 |

Product Composition (Mol %)

[a]Except as noted decene-5 only detected
[b]Isoundecyl aldehydes consisting of 2-n-butylheptanal (≧ 90) and varying amounts of 2-n-propyloctanal, 2-ethylnonal and 2-methyldecanal were obtained.
[c]Decene-5 isomers detected
[d]After partial deactivation of the catalyst on repeated use, the solid was extensively washed prior to Experiment 8 to remove accumulated poisons.

Consecutive Batch Hydroformylation of Decene-5 with the Same Sample of γ-Alumina-Supported Chlororhodium Phthalocyanine Tetrasulfonate The reaction products were subsequently analyzed by gas-liquid chromatography instrumentation for rhodium metal content, said analysis indicated only trace amounts of the rhodium metal. The lack of rhodium metal content in the final products verifies the heterogeneous physical nature of the catalyst and the feasibility of metal recovery.

EXAMPLE IV

The chlororhodium phthalocyanine tetrasulfonate prepared as indicated in Example II was tested for hydroformylation activity using decene-5 as a test olefin in a series of consecutive, batch experiments with the chlororhodium phthalocyanine tetrasulfonate in an aqueous dispersion. In Example IV the same sample of chlororhodium phthalocyanine tetrasulfonate (0.1 g., 0.09 mmols) was weighed into an 850 ml, glass lined, rotating, stainless steel autoclave along with decene-5 and some water. The decene-5 and aqueous chlororhodium phthalocyanine tetrasulfonate formed a two phase catalyst-reactant system. After the autoclave was flushed with nitrogen, sealed, pressurized to the designated carbon monoxide-hydrogen pressures and heated with rotation to 80° C. for an 18-hour period of time, the rotation was stopped and the autoclave allowed to return to room temperature after termination of heat. The autoclave was then flushed with nitrogen to remove any residual carbon monoxide and the two phase catalyst-product system which resulted was separated by pouring off the product. The aqueous catalyst phase was washed free of decene-hydroformylation products with pentane before it was charged to another experiment. The non-aqueous products were analyzed by gas-liquid chromatographic instrumentation after each consecutive run, said analyses disclosed the presence of the percentages of oxo-aldehydes indicated in Table II below:

EXAMPLE V

In this example 5.08 grams of rhodium trichloride hydrate (0.0195 mmols of rhodium) and a small amount of ammonium molybdate were dissolved in 25 mls of water. The solution was mixed with 21.1 grams (0.1 mols) of 4-nitrophthalic acid in about 50 ml of water resulting in a red-brown mush into which was stirred 33.0 grams (0.55 mols) of urea. The resultant red-brown solid was heated to a temperature of 120° C. which created frothing and gas evolution. The product was heated further to a temperature of 180° C. to 185° C. for a period of time comprising 1 hour at which time 75 mls of trichlorobenzene was added to moderate the temperature. The heating was continued at temperatures of 185° C. to 210° C. for a period of time comprising 90 minutes after which heating was terminated to the mixture. The resultant dark green product was recovered by filtration, washed with benzene and found to be 30.9 grams of crude chlororhodium tetranitrophthalocyanine. The crude chlororhodium tetranitrophthalocyanine was washed with water and reduced to chlororhodium tetraaminophthalocyanine by treating with tin and hydrochloric acid. For purposes of the reduction, 3.0 grams (3.52 mmols) of water washed chlororhodium tetranitrophthalocyanine was reacted with 1.78 grams (15.1 mmols) of tin and excess hydrochloric acid at 75° C. to 80° C. for about one hour. A small portion of the resultant solution was evaporated to give a deep green product which was analyzed by infrared spectroscopy, said analysis disclosed the presence of chlororhodium tetraaminophthalocyanine. The chlororhodium tetraaminophthalocyanine was impregnated upon 25 ml of silica-gel by pouring the silica-gel directly into the remaining dispersion and recovering the silica impregnated with chlororhodium tetraaminophthalocyanine by filtration. The resultant

TABLE II

| Experiment | Initial Pressure CO/H₂ Atm | Mmols Decene-5 Charged | Grams Water Charged | Decane | Decene-5 | Isoundecyl Aldehydes | Undecanal |
|---|---|---|---|---|---|---|---|
| 1 | 80/80 | 136 | 2 | 0.5 | 0 | 95.3 | 1.9 |
| 2 | 80/80 | 150 | 5 | 0 | 1.1 | 97.8 | 1.1 |
| 3 | 80/80 | 150 | 2 | trace | 9.8 | 90.2 | 0 |
| 4 | 60/60 | 129 | 2 | trace | 9.4 | 90.5 | 0 |

Non-Aqueous Product Composition — Mol %

Consecutive-Batch Hydroformylation of Decene-5 with the Same Sample of Chlororhodium Phthalocyanine Tetrasulfonate in a Two Phase Catalyst-Reactant System green catalyst comprising silica-supported chlororhodium tetraaminophthalocyanine was washed with water and air dried.

In Example V, 143.0 mmols of decene-5 and the silica-supported chlororhodium tetraaminophthalocyanine were added to an 850 ml glass lined rotating stainless steel autoclave which was flushed with nitrogen and subsequently sealed. Carbon monoxide was charged to an initial pressure of 80 atmospheres of carbon monoxide and hydrogen was charged to an initial pressure of 80 atmospheres, said total pressure being 160 atmospheres. The autoclave was then rotated and heated to a temperature of 80° C. and maintaind thereat for a period of time comprising 18 hours. After the passage of the 18-hour period of time, the rotation of the autoclave was stopped and it was allowed to return to room temperature after the termination of heat, vented in a fume hood and flushed with nitrogen to remove any residual carbon monoxide. The reaction product was recovered from the autoclave and analyzed by gas-liquid chromatography instrumentation, said analysis disclosed the presence of 81.3% of 2-butylheptanal.

EXAMPLE VI

In this example 1.0 grams of cobalt phthalocyanine (1.75 mmols of cobalt) was added to an 850 ml glass lined rotating stainless steel autoclave which was flushed with nitrogen and subsequently sealed. Then about 500 mmols of propylene was charged to the autoclave by means of a pressurized calibrated charging vessel. Carbon monoxide was charged to the initial carbon monoxide pressure of 120 atmospheres and hydrogen was charged to an initial hydrogen pressure of 120 atmospheres, said total pressure being 240 atmospheres. The autoclave was rotated and heated to a temperature of 160° C. and maintained thereat for a period of time comprising 8 hours. After passage of the 8-hour period of time, the autoclave rotation was stopped and it was allowed to return to room temperature after the termination of heat. The autoclave was vented in a fume hood and flushed with nitrogen to remove any residual carbon monoxide. The reaction product was recovered from the autoclave and analyzed by means of gas-liquid chromatography instrumentation and infrared spectroscopy, said analyses disclosed the reaction product to by approximately 280 mmols of isobutyraldehyde (46 mol%) and n-butanal (54 mol%).

EXAMPLE VII

In this example a continuous liquid-liquid reaction system is maintained by means of an iridium phthalocyanine tetrasulfonate dissolved in water in one phase and tetradecene-7 in a solution with normal pentane in a second liquid phase. The liquid-liquid hydroformylation system is maintained at a temperature of 25° C. and a pressure of 50 atmospheres of carbon monoxide and 50 atmospheres of hydrogen. The contact time between the liquid-liquid phases is determined by the interface of the liquid-liquid solution which in turn is determined by proper stirring mechanisms. The liquid-liquid system is stirred at a rate equal to the contact time of the unsaturated compound with the catalyst composition of matter phase of 0.5 hours. The reaction product is recovered as the effluent from the liquid-liquid reactant catalyst phase system and found to be 2-n-amyldecanal.

EXAMPLE VIII

In this example a catalyst system comprising ruthenium phthalocyanine disulfonate in a similar liquid-liquid system of Example IV is maintained in the hydroformylation of heptene-3. The reaction product in this example is found to be 3-n-propylpentanol.

I claim:
1. In a process for the hydroformylation of an unsaturated compound which is reactable with carbon monoxide and hydrogen to form an alcohol or aldehyde, wherein said unsaturated compound is reacted with carbon monoxide and hydrogen at a temperature of from about 15°C to about 300°C and a pressure of from about atmospheric to about 500 atmospheres, the improvement of effecting the hydroformylation reaction in the presence of a phthalocyanine of a metal selected from the group consisting of rhenium, rhodium, cobalt, ruthenium, iridium and osmium, said phthalocyanine being in an amount of from about 0.00001 to about 10.0 mols per mol of said unsaturated compound.

2. The process of claim 1 further characterized in that said unsaturated compound is an olefinic hydrocarbon of from about 3 to 30 carbon atoms.

3. The process of claim 2 further characterized in that said olefinic hydrocarbon is decene-5.

4. The process claim 2 further characterized in that said olefinic hydrocarbon is tetradecene-7.

5. The process of claim 2 further characterized in that said olefinic hydrocarbon is heptene-3.

6. The process of claim 2 further characterized in that said olefinic hydrocarbon is propylene.

7. The process of claim 1 further characterized in that said phthalocyanine is chlororhodium phthalocyanine.

8. The process of claim 1 further characterized in that said phthalocyanine is chlororhenium phthalocyanine.

9. The process of claim 1 further characterized in that said phthalocyanine is cobalt phthalocyanine.

10. The process of claim 1 further characterized in that said phthalocyanine is iridium phthalocyanine.

11. The process of claim 1 further characterized in that said phthalocyanine is ruthenium phthalocyanine.

* * * * *